United States Patent
Leroux et al.

(10) Patent No.: US 12,335,692 B2
(45) Date of Patent: Jun. 17, 2025

(54) IMPLANTABLE TINNITUS THERAPY

(71) Applicant: Cochlear Limited, Macquarie University (AU)

(72) Inventors: Thomas Leroux, Macquarie University (AU); Olivier Le Caharec, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 507 days.

(21) Appl. No.: 17/798,782

(22) PCT Filed: Jan. 20, 2021

(86) PCT No.: PCT/IB2021/050426
§ 371 (c)(1),
(2) Date: Aug. 10, 2022

(87) PCT Pub. No.: WO2021/165759
PCT Pub. Date: Aug. 26, 2021

(65) Prior Publication Data
US 2023/0110745 A1    Apr. 13, 2023

Related U.S. Application Data

(60) Provisional application No. 62/979,501, filed on Feb. 21, 2020.

(51) Int. Cl.
*H04R 25/00* (2006.01)
*A61N 1/02* (2006.01)
*A61N 1/36* (2006.01)

(52) U.S. Cl.
CPC ............ *H04R 25/75* (2013.01); *A61N 1/025* (2013.01); *A61N 1/36036* (2017.08); *A61N 1/36132* (2013.01)

(58) Field of Classification Search
CPC .... H04R 25/75; A61N 1/36036; A61N 1/025; A61N 1/36132
See application file for complete search history.

(56) References Cited

U.S. PATENT DOCUMENTS

| | | |
|---|---|---|
| 5,795,287 A | 8/1998 | Ball et al. |
| 6,251,062 B1 | 6/2001 | Leysieffer |

(Continued)

FOREIGN PATENT DOCUMENTS

| | | |
|---|---|---|
| KR | 10-1517143 B1 | 5/2015 |
| KR | 10-2017-0129689 A | 11/2017 |

(Continued)

OTHER PUBLICATIONS

International Search Report and Written Opinion in counterpart International Application No. PCT/IB2021/050426, mailed Apr. 26, 2021, 10 pages.

*Primary Examiner* — Mark Fischer
(74) *Attorney, Agent, or Firm* — Edell, Shapiro & Finnan, LLC

(57) ABSTRACT

Presented herein are techniques for providing tinnitus relief to recipients via an implantable arrangement. In accordance with embodiments presented herein, an implantable medical device, such as implantable tinnitus therapy device, auditory/hearing prosthesis, etc., comprises one or more implantable sensors configured to be implanted in a recipient. The one or more implantable sensors are configured to detect body noises of the recipient. The implantable medical device is configured to classify/categorize the one or more body noises and set, select, or otherwise determine a tinnitus therapy for the recipient based on the classification of the one or more body noises.

20 Claims, 9 Drawing Sheets

(56) References Cited

U.S. PATENT DOCUMENTS

| | | | |
|---|---|---|---|
| 6,565,503 | B2 | 5/2003 | Leysieffer et al. |
| 6,575,894 | B2 | 6/2003 | Leysieffer et al. |
| 7,442,164 | B2 | 10/2008 | Berrang et al. |
| 9,143,873 | B2 | 9/2015 | Abolfathi |
| 10,225,671 | B2 | 3/2019 | Goorevich et al. |
| 2007/0021804 | A1 | 1/2007 | Maltan et al. |
| 2007/0203536 | A1 | 8/2007 | Hochmair et al. |
| 2009/0270673 | A1 | 10/2009 | Abolfath et al. |
| 2013/0039517 | A1 | 2/2013 | Nielsen et al. |
| 2016/0094923 | A1 | 3/2016 | Jensen et al. |
| 2016/0323683 | A1 | 11/2016 | Pontoppidan |
| 2019/0054305 | A1 | 2/2019 | Janssen et al. |

FOREIGN PATENT DOCUMENTS

| | | |
|---|---|---|
| WO | 2017213978 A1 | 12/2017 |
| WO | 2019-161277 A1 | 8/2019 |

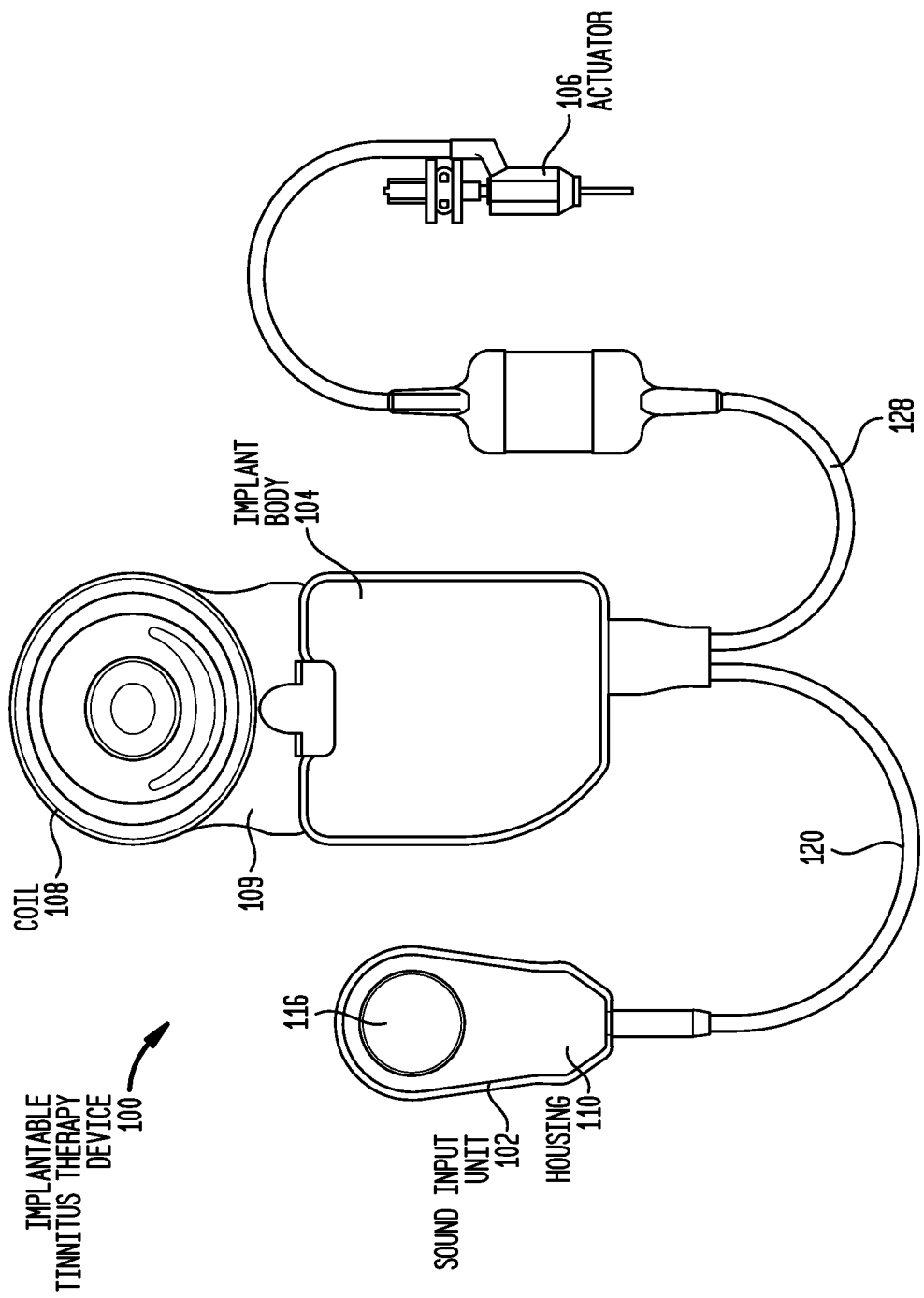

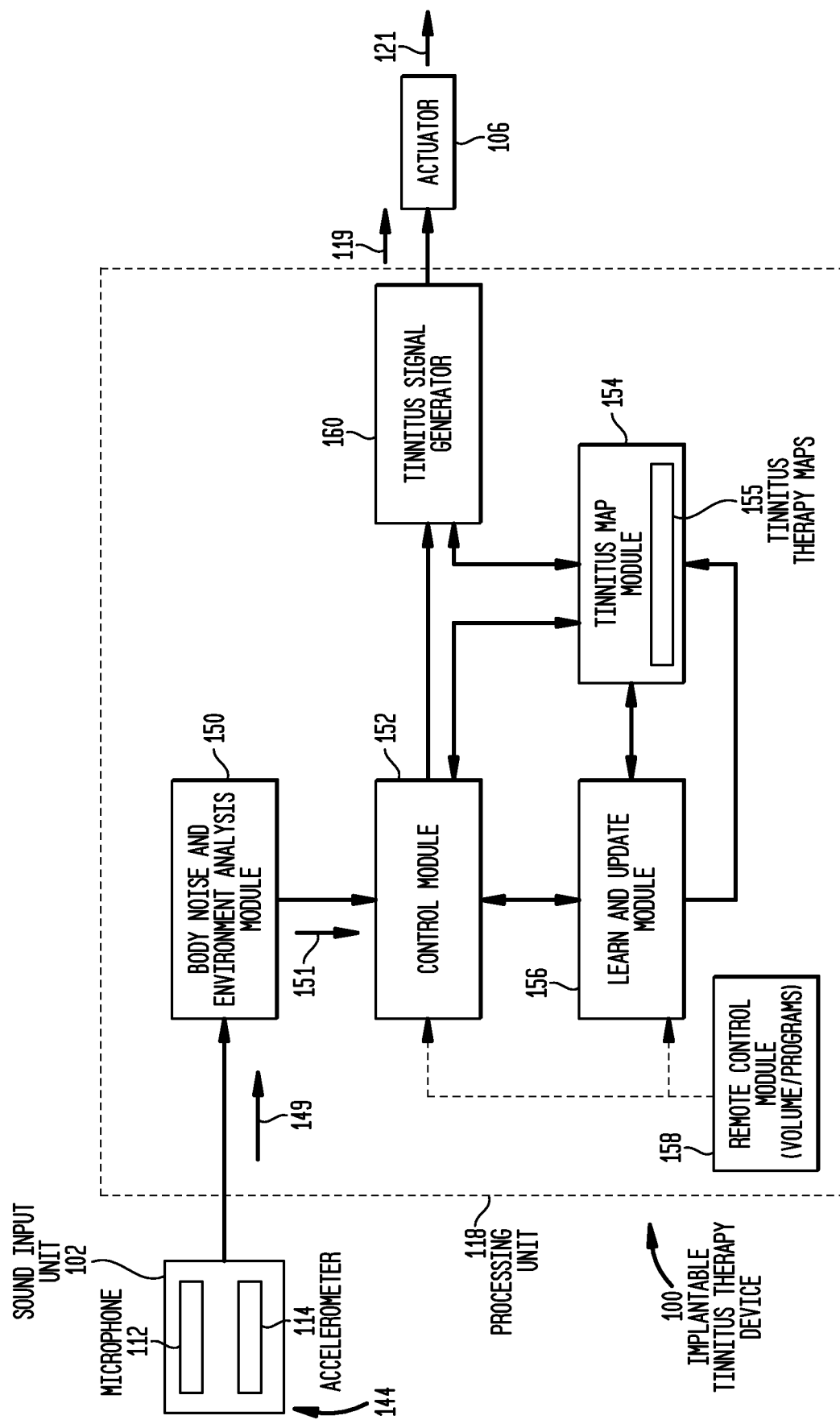

IMPLANTABLE TINNITUS THERAPY

BACKGROUND

Field of the Invention

The present invention relates generally to tinnitus therapy with an implantable medical device.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a method is provided. The method comprises: detecting signals at one or more implantable sensors configured to be implanted in a recipient, wherein the signals comprise one or more body noises of the recipient; generating, based on the one or more body noises, one or more body noise classifications; generating tinnitus therapy signals based on the one or more body noise classifications; and delivering the tinnitus therapy signals to the recipient.

In another aspect, an apparatus is provided. The apparatus comprises: one or more implantable sensors configured to be implanted in a recipient, wherein the one or more implantable sensors are configured to detect one or more body noises of the recipient; a processing unit configured to: generate, based on the one or more body noises, one or more body noise classifications, and generate actuator control signals based on the body noise classifications; and an implantable actuator configured to deliver tinnitus therapy signals to the recipient based on the actuator control signals.

In another aspect, a method is provided. The method comprises: detecting one or more body noises at one or more implantable sensors configured to be implanted in a recipient; categorizing the one or more body noises; and controlling a tinnitus therapy for the recipient as a function of the categorization of the one or more body noises.

In another aspect, one or more non-transitory computer readable storage media comprising instructions are provided. The instructions, when executed by a processor, cause the processor to: identify one or more body noises in signals captured by one or more implantable sensors of an implantable medical device; generate one or more body noise classifications based on the one or more body noises; and generate tinnitus therapy control signals based on the one or more body noise classifications.

In another aspect, an apparatus is provided. The apparatus comprises: at least one microphone configured to be implanted in a recipient, wherein the microphone is configured to detect one or more external acoustic sounds; at least one accelerometer configured to be implanted in the recipient, wherein the accelerometer is configured to detect one or more body noises of the recipient; an implantable actuator rigidly coupled to the recipient so as to directly or indirectly deliver vibration to a cochlea of the recipient; and one or more processors configured to separately categorize the one or more external acoustic sounds and the one or more body noises and to generate actuator control signals based on the categorization of the one or more external acoustic sounds and the one or more body noises, wherein the actuator is configured to vibrate based on the actuator control signals to deliver tinnitus therapy signals to the recipient based on the actuator control signals.

BRIEF DESCRIPTION OF THE DRAWINGS

Embodiments of the present invention are described herein in conjunction with the accompanying drawings, in which:

FIG. 1A is a top view of a totally implantable tinnitus therapy device, in accordance with certain embodiments presented herein;

FIG. 2 is a functional block diagram of a processing unit of an implantable tinnitus therapy device, in accordance with certain embodiments presented herein;

DETAILED DESCRIPTION

Tinnitus is the perception of noise or "ringing" in the ears which currently affects an estimated 30 million people in the United States alone. Tinnitus is a common artefact of hearing loss, but can also be a symptom of other underlying conditions, such as ear injuries, circulatory system disorders, etc. Although tinnitus affects can range from mild to severe, almost one-quarter of those with tinnitus describe their tinnitus as disabling or nearly disabling.

Presented herein are techniques for providing tinnitus relief to recipients via an implantable arrangement. In accordance with embodiments presented herein, an implantable medical device, such as implantable tinnitus therapy device, auditory/hearing prosthesis, etc., comprises one or more implantable sensors configured to be implanted in a recipient. The one or more implantable sensors are configured to detect body noises of the recipient. The implantable medical device is configured to classify/categorize the one or more body noises and set, select, or otherwise determine a tinnitus therapy for the recipient based on the classification of the one or more body noises.

Merely for ease of description, the tinnitus therapy techniques presented herein are primarily described herein with reference to a so-called "stand-alone" implantable tinnitus therapy device, sometimes referred to herein as a tinnitus therapy device or tinnitus relief device. As used herein, a tinnitus therapy or tinnitus relief device is an implantable medical device having a primary purpose of providing tinnitus therapy/relief to a recipient. However, it is to be appreciated that the techniques presented herein can also be incorporated into, or performed by, a variety of other implantable medical devices. For example, the techniques presented herein can be used with other auditory prostheses, including cochlear implants, bone conduction devices, middle ear auditory prostheses, direct acoustic stimulators, auditory brain stimulators), etc. The techniques presented herein can also be used with vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 1B:
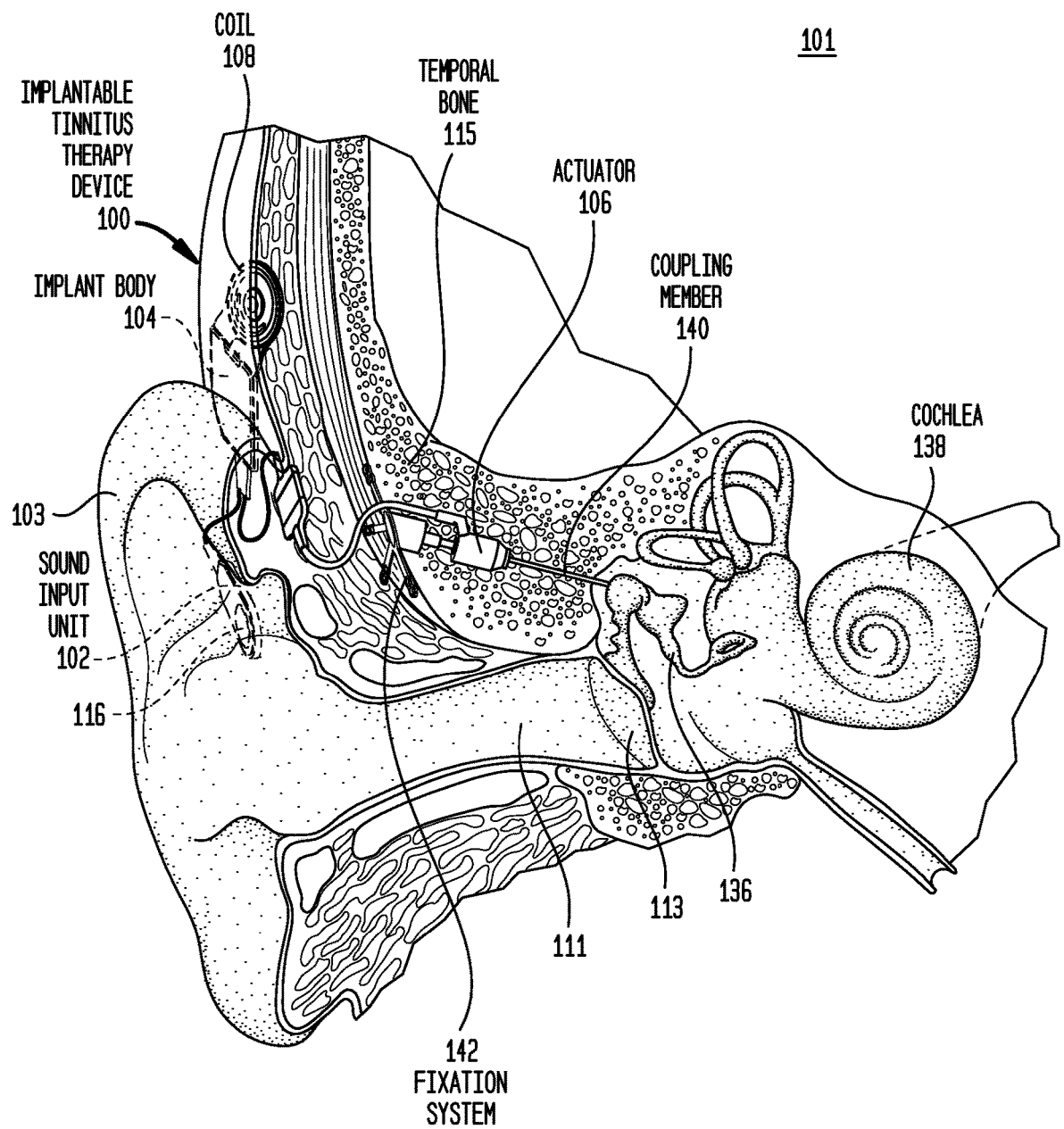
FIG. 1B is a schematic diagram illustrating the totally implantable tinnitus therapy device of FIG. 1A implanted within the head of a recipient, in accordance with certain embodiments presented herein.
Figure 1C:
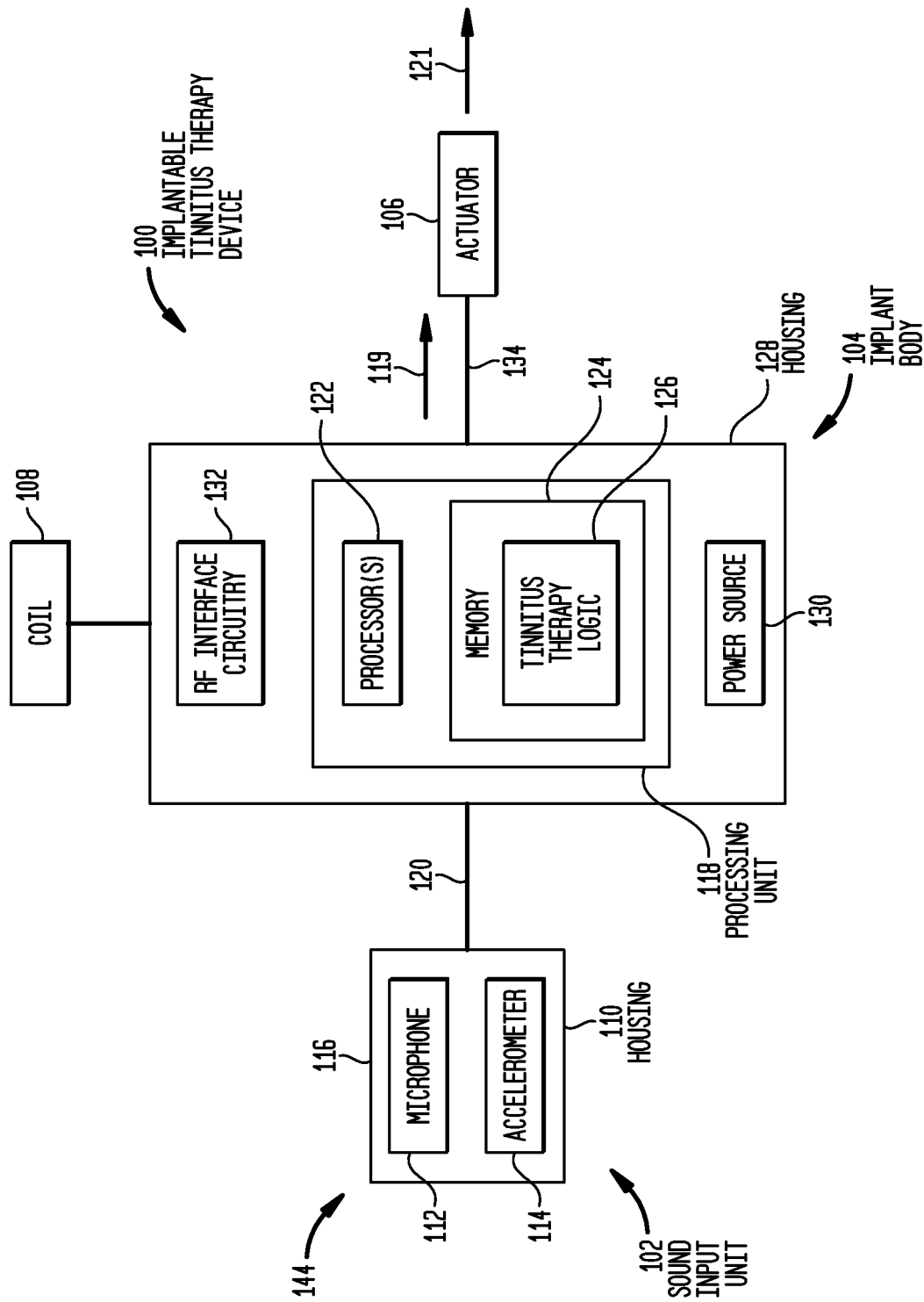
FIG. 1C is a functional block diagram of the totally implantable tinnitus therapy device of FIG. 1A, in accordance with certain embodiments presented herein.

FIG. 1A is a top view of an implantable tinnitus therapy device 100, in accordance with certain embodiments presented herein. FIG. 1B is schematic diagram illustrating the implantable tinnitus therapy device 100 of FIG. 1A implanted in a recipient 10, while FIG. 1C is a schematic block diagram of the implantable tinnitus therapy device 100. For ease of description, FIGS. 1A-1C will be described together.

The implantable tinnitus therapy device 100 of FIGS. 1A-1C comprises a sound input unit 102, an implant body 104, an actuator 106, and a coil 108, all implanted under the skin/tissue of the recipient 101. The sound input unit 102 comprises a substantially rigid housing 110, in which at least two implantable sensors 112 and 114 are disposed/positioned. The implantable sensor 112 is more sensitive to external acoustic sounds than it is to body noises, while implantable sensor 114 is more sensitive to body noises than it is to external acoustic sound signals. That is, the implantable sensor 112 is a "sound" sensor/transducer that is primarily configured to detect/receive external acoustic sounds (e.g., an implantable microphone), while the implantable sensor 114 is a "vibration" sensor that is primarily configured to detect/receive internal body noises (e.g., another implantable microphone or an accelerometer). The increased sensitivity of the sensor 114 to body noise can be due to, for example, the structure of the sensor 114 relative to the sensor 112, the implanted position of the sensor 114 relative to the sensor 112, etc. For ease of reference, the microphone 112 and the accelerometer 114 are sometimes collectively referred to herein as "implantable sensors" 144.

For ease of description, embodiments presented herein will be primarily described with reference to the use of an implantable microphone 112 as the sound sensor and an accelerometer 114 as the vibration sensor. However, it is to be appreciated that these specific implementations are non-limiting and that embodiments of the present invention can be used with different types of implantable sensors.

The housing 110 is hermetically sealed and includes a diaphragm 116 that is proximate to the microphone 112. The diaphragm 116 can be unitary with the housing 116 and/or can be a separate element that is attached (e.g., welded) to the housing 112. The sound input unit 102 is configured to be implanted within the recipient 101. In one example shown in FIG. 1B, the sound input unit 102 is configured to be implanted within the skin/tissue adjacent to the outer ear 103 of the recipient. In this position, the diaphragm 116 is below the skin of the recipient that is close to the recipient's ear canal 105. In operation, sound signals that impinge on the skin adjacent to (i.e., on top of) the diaphragm 116 cause the skin adjacent the diaphragm 116, and thus the diaphragm 116 itself, to be displaced (vibrate) in response to the sound signals. The displacement of the diaphragm 116 is detected by the microphone 112. In this way, the microphone 112, although implanted within the recipient, is able to detect external acoustic sound signals (external acoustic sounds).

In the example of FIGS. 1A-1C, the implantable microphone 112 and the accelerometer 114 can each be electrically connected to the implant body 104 (e.g., in a separate casing connected to the main implant body 104). Alternatively, the implantable microphone 112 and the accelerometer 114 can be integrated in the main implant body 104. In operation, the microphone 112 and the accelerometer 114 detect input (sound/vibration) signals (e.g., external acoustic sounds and/or body noises) and convert the detected input signals into electrical signals that are provided to the processing unit 118 (e.g., via lead 120). As described further below, the processing unit 118 is configured to identify and classify/categorize body noises detected by the accelerometer 114 and/or microphone 112. The processing unit 118 is configured to generate tinnitus therapy control signals 119 (FIG. 1C) based at least on identified body noises detected by the accelerometer 114 and/or microphone 112. Also as described further below, in certain examples the processing unit 118 is further configured to generate the tinnitus therapy control signals based the identified body noises and based on an acoustic environment of the recipient (e.g., based on a classification of the body noises and based on a classification of acoustic sound signals detected by the accelerometer 114 and/or microphone 112).

In the example of FIG. 1B, the processing unit 118 comprises at least one processor 122 and memory 124. The memory 124 includes tinnitus therapy logic 126 that, when executed by the at least one processor 122, cause the at least one processor 122 to perform the tinnitus therapy operations described herein (e.g., identify one or more body noises in signals captured by the implantable sensors, classify the one or more body noises, and generate tinnitus therapy control signals based at least on identified body noises). Memory 124 can comprise any suitable volatile or non-volatile computer readable storage media including, for example, random access memory (RAM), cache memory, persistent storage (e.g., semiconductor storage device, read-only memory (ROM), erasable programmable read-only memory (EPROM), flash memory, etc.), or any other computer readable storage media that is capable of storing program instructions or digital information. The processing unit 118 can be implemented, for example, on one or more printed circuit boards (PCBs).

It is to be appreciated that the arrangement for processing unit 118 in FIG. 1C is merely illustrative and that the tinnitus therapy techniques presented herein can be implemented with a number of different processing arrangements. For example, the tinnitus therapy techniques herein can be implemented with processing units formed by any of, or a combination of, one or more processors (e.g., one or more Digital Signal Processors (DSPs), one or more uC cores, etc.), firmware, software, etc. arranged to perform, for example, the operations described herein.

As shown, the implant body 114 includes a hermetically sealed housing 128 in which the processing unit 118 is disposed. Also disposed in the housing 128 is a power source (e.g., rechargeable battery) 130 and a radio-frequency (RF) interface circuitry 132. Electrically connected to the RF interface circuitry 132 is the implantable coil 108, which is disposed outside of the housing 128. Implantable coil 108 is typically a wire antenna coil comprised of multiple turns of electrically insulated single-strand or multi-strand platinum or gold wire. The electrical insulation of implantable coil 108 is provided by a flexible molding (e.g., silicone molding) 109 (FIG. 1A). In general, the implantable coil 108 and the RF interface circuitry 132 enable the receipt of power and data from an external device (not shown in FIGS. 1A-1C) and, potentially, the transfer of data to an external device. However, it is to be appreciated that various types of energy transfer, such as infrared (IR), electromagnetic, capacitive and inductive transfer, can be used to transfer power and/or data from an external device and, as such, FIG. 1B illustrates only one example arrangement.

In certain example, the external device can comprise an off-the-ear (OTE) unit that is configured to send data, and potentially power, to the implantable tinnitus therapy device 100. In general, an OTE unit is a component having a generally cylindrical shape and which is configured to be magnetically coupled to the recipient's head. The OTE unit also includes an integrated external coil that is configured to be inductively coupled to the implantable coil 108. In alternative examples, the external device can comprise a behind-the-ear (BTE) unit or a micro-BTE unit, configured to be worn adjacent to the recipient's outer ear. In general, a BTE unit comprises a housing that is shaped to be worn on the outer ear of the recipient and is connected to a separate external coil configured to be inductively coupled to the implantable coil 108.

It is to be appreciated that OTE units and BTE units are merely illustrative of the external devices that can operate with an implantable tinnitus therapy device, such as device 100, in accordance with embodiments presented herein. Alternative external devices can be located in the recipient's ear canal, a body-worn, a consumer electronic device (e.g., mobile phone communication with implantable tinnitus therapy device via a wireless link), etc. For example, in certain embodiments, the implant body 104 can also include a short-range wireless interface for communication with external devices. The short-range wireless interface can be, for example, as Bluetooth® interface, Bluetooth® Low Energy (BLE) interface, or other interface making use of any number of standard or proprietary protocols. Bluetooth® is a registered trademark owned by the Bluetooth® SIG.

Returning to the example of FIGS. 1A-1C, as noted above, the processing unit 118 generates tinnitus therapy control signals 119. The tinnitus therapy control signals 119 are provided to the actuator 106 (e.g., via lead 134) for use in delivering tinnitus therapy signals (tinnitus therapy) to the recipient. In FIG. 1C, the tinnitus therapy signals delivered to the recipient are represented by arrow 121.

In the example of FIG. 1B, the actuator 106 delivers the tinnitus therapy signals 121 to the recipient via the ossicular chain (ossicles) 136 (i.e., the bones of the middle ear, which comprise the malleus, the incus and the stapes). The ossicles 136 are positioned in the middle ear cavity 113 and are mechanically coupled between the tympanic membrane 113 and the oval window (not shown) of cochlea 138. In natural hearing, the ossicles 136 serve to filter and amplify sound waves received via the recipient's ear canal 111, causing oval window to articulate (vibrate) in response to the vibration of tympanic membrane 113. This vibration of the oval window sets up waves of fluid motion of the perilymph within cochlea 138. Such fluid motion, in turn, activates tiny hair cells (not shown) inside of cochlea 138. Activation of the hair cells causes appropriate nerve impulses to be generated and transferred through the spiral ganglion cells (not shown) and auditory nerve (not shown) to the brain (also not shown), where they are perceived as sound.

Figure 1D:
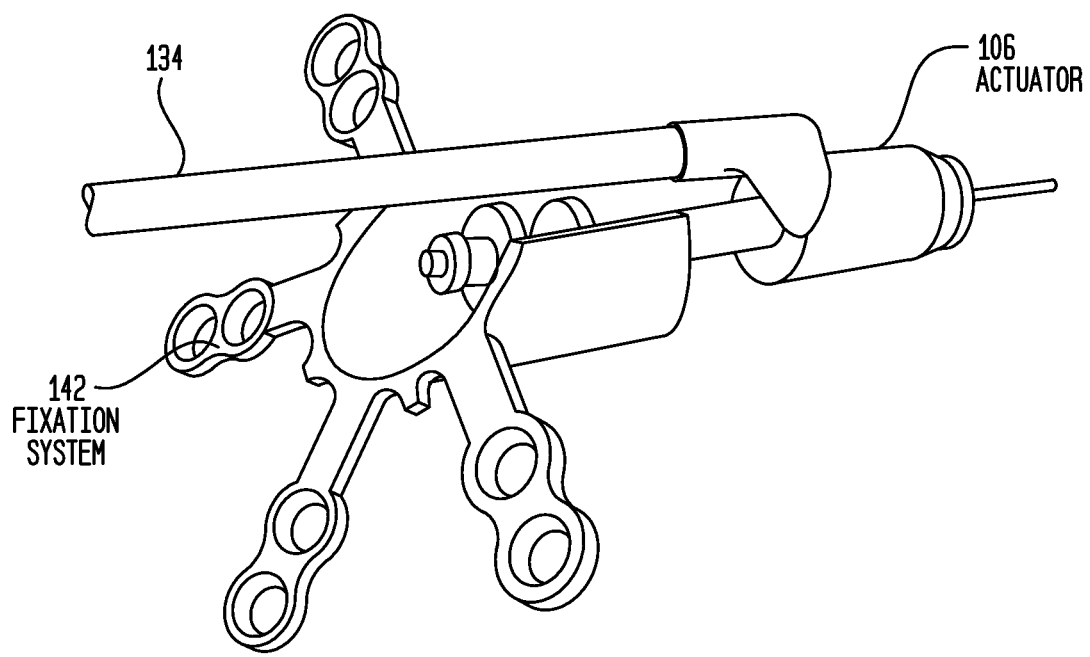
FIG. 1D is a perspective view of an actuator of the totally implantable tinnitus therapy device of FIG. 1A and a fixation system, in accordance with certain embodiments presented herein.
Figure 1E:
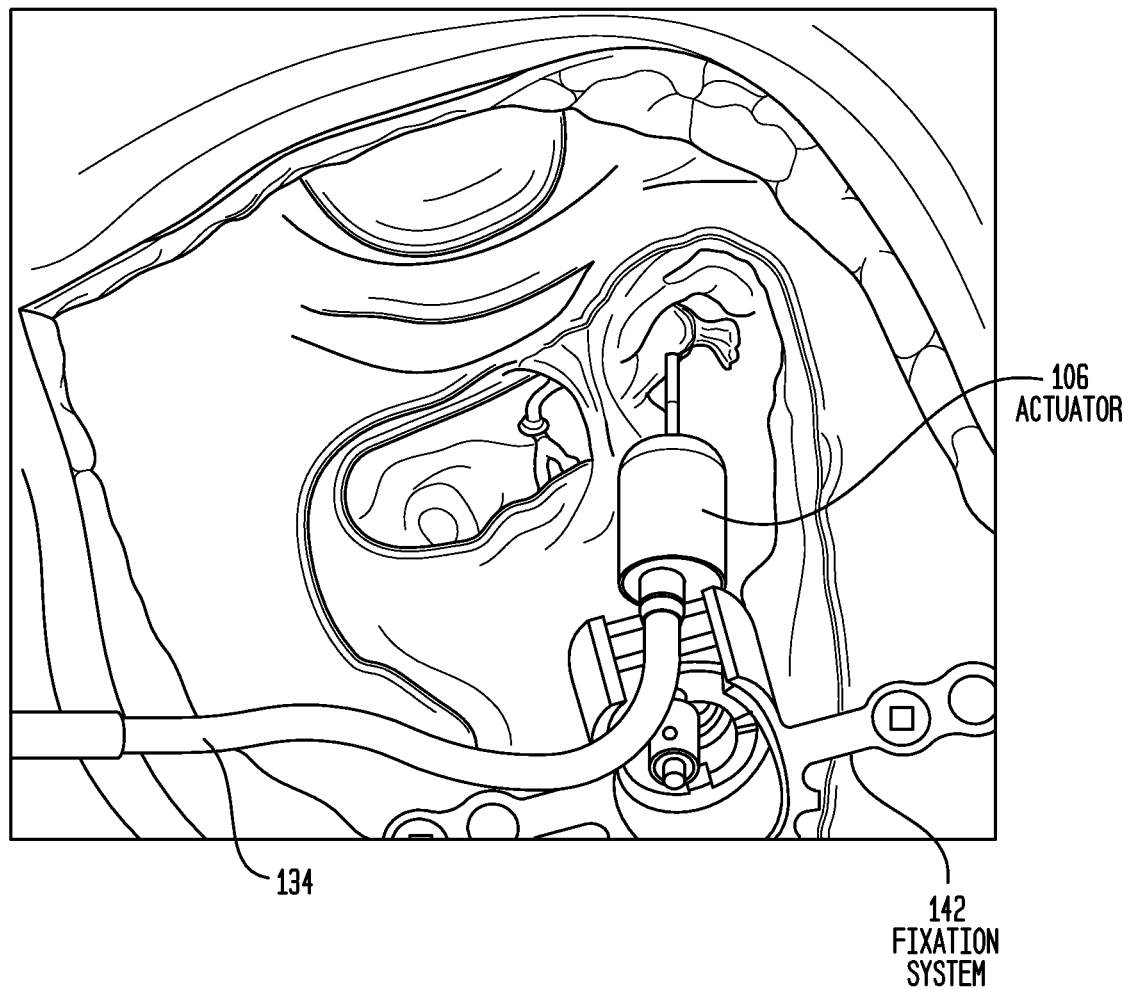
FIG. 1E is another perspective view of the actuator and fixation system of FIG. 1D, in accordance with certain embodiments presented herein.

As shown in FIG. 1B, the actuator 106 is configured to be implanted in the recipient so as to impart motion to (e.g., vibrate) the ossicles 136. In FIG. 1B, the actuator 106 attached to the bone 115 of the recipient via a fixation system 142 (also shown in more detail in FIGS. 1D and 1E). In addition, the actuator 106 is mechanically coupled to the ossicles 136 (e.g., the incus) via a coupling member 140, which can be part of the actuator 106 and/or a separate element attached to the actuator.

In operation, the actuator 106 is configured to generate vibration (vibration signals 121) based on the tinnitus therapy control signals 119 received from the processing unit 118. Since, as noted, the ossicles 136 are coupled to the oval window (not shown) of cochlea 138, vibration imparted to the ossicles 136 by the actuator 106 will, in turn, cause oval window to articulate (vibrate) in response thereto. Similar to the case with normal hearing, this vibration of the oval window sets up waves of fluid motion of the perilymph within cochlea 138 which, in turn, activates the hair cells inside of the cochlea 138. Activation of the hair cells causes appropriate nerve impulses to be generated and transferred through the spiral ganglion cells (not shown) and auditory nerve (not shown) to the brain (also not shown), where they are perceived as sounds that, as described below, provide relief of tinnitus symptoms experienced by the recipient.

As noted, FIG. 1B illustrates an arrangement in which the actuator 106 is mechanically coupled to the ossicles 136 via coupling member 140. In certain embodiments, such as a stand-alone tinnitus therapy device embodiment, the coupling between actuator 106 and the ossicles 136 is sufficiently rigid so as to enable the delivery of the tinnitus therapy signals to the ossicles 136, but is also configured so as to have no or only minimal negative effects on the recipient's natural hearing capabilities, thereby making the actuator 106 and coupling member 140 useable for recipient's with normal hearing (e.g., no or minimal hearing loss).

It is to be appreciated that the arrangement shown in FIG. 1B in which the actuator 106 is mechanically coupled to the ossicles 136 is merely illustrative and that the tinnitus therapy techniques presented herein can be used with different mechanical stimulation arrangements. For example, in alternative embodiments, the actuator 106 can be coupled directly to the oval window, another opening in the cochlea 138 (e.g., a cochleostomy or the round window), an opening in the recipient's semicircular canals, etc.

FIG. 2 is a functional block diagram illustrating further details of the tinnitus therapy techniques presented herein. For ease of description, FIG. 2 will be described with reference to the arrangement shown in FIGS. 1A-1E.

In particular, shown in FIG. 2 is the sound input unit 102, the actuator 106, and a functional representation of the processing unit 118. In this example, the processing unit 118 is represented as a plurality of functional modules, including body noise and environment analysis module 150, control module 152, tinnitus map module 154, learn and update module 156, remote control module 158, and tinnitus signal generator 160. It is to be appreciated that the functional arrangement shown in FIG. 2 is merely illustrative and does not require or imply any specific structural arrangements. Three various functional modules shown in FIG. 2 can be implemented in any combination of hardware, software, firmware, etc.

Returning to the example of FIG. 2, the sound input unit 102 includes implantable sensors 144 (e.g., microphone 112 and accelerometer 114), which are configured to detect/receive external acoustic sound signals and/or body noises. As used herein, external acoustic sound signals (external acoustic sounds) are sound signals (sounds) that originate from outside of the recipient's body. In contrast, body noises are sounds induced by the body (i.e., originating inside the body of the recipient) that are propagated primarily as vibration, such as breathing, scratching, rubbing, noises associated with the movement of the head, chewing, etc. Own voice (OV) (i.e., when the recipient speaks) is a particular case of body noise since the sound is transmitted both through air conduction and bone conduction (i.e., skull vibrations). In certain own voice instances, most of these sound propagates through the skull bones and produce accelerations at the implantable microphone. That is, in general, body noises that can be characterized as an acceleration coming from the body (or the recipient's own voice), and captured by the implantable sensors 144.

The sounds detected by the implantable sensors (either external acoustic sound signals or body noises) are converted into electrical input signals, which are represented in FIG. 2 by arrow 149. As shown, the sound input unit 102 provides the electrical input signals 149 to the body noise and environment analysis module 150. The body noise and environment analysis module 150 can be configured to perform a number of operations based on the electrical input signals 149.

In particular, the body noise and environment analysis module 150 is configured to identify and "classify" or "categorize" the body noise(s) present in the electrical input signals 149 provided by the implantable sensors 144. That is, using the electrical input signals 149, the body noise and environment analysis module 150 is configured to identify any body noises that are present and evaluate/analyze the received body noises to determine the class/category/of the body noises.

A classification of the body noise(s), referred to herein as a "body noise classification," by the body noise and environment analysis module 150 can take any of a number of different forms. For example, the body noise classification can indicate a current estimated activity or behavior of the recipient, such as "sleeping," "snoring," "eating," "chewing," "speaking" (i.e., own-voice detection), etc. (i.e., a body noise-based activity classification). The body noise classifications can also indicate current background body noises, including "breathing," "heartbeat," "swallowing," etc. In addition, the body noise classifications can indicate emotional reactions (emotions) of the recipient (e.g., stress, anxiety, etc.). The body noise classifications can also provide qualitative indications of the recipient's current estimated activities or background body noises, such as "low heartrate," "deep breathing," "shallow breathing," "deep sleep," etc.

In accordance with certain embodiments presented herein, the body noise and environment analysis module 150 can make multiple simultaneous classifications of a recipient's body noise(s) (i.e., simultaneously classify the same electrical input signals generated based on the same signals captured within a time period in different manners). For example, the body noise and environment analysis module 150 can simultaneously classify body noise(s) as "low heartrate" and "deep breathing."

In addition to generating body noise classifications, the body noise and environment analysis module 150 can also be configured to use the electrical input signals 149 to "classify" or "categorize" the ambient sound environment of the tinnitus therapy device 100 (i.e., classify the external acoustic sounds detected by the implantable sensors 144). The classification of the ambient environment, sometimes referred to herein as an "environment classification," can include, but are not limited to, "Speech" (e.g., the sound signals include primarily speech signals), "Noise" (e.g., the sound signals include primarily noise signals), "Speech+Noise" (e.g., both speech and noise are present in the sound signals), "Wind" (e.g., e.g., the sound signals include primarily wind signals), "Music" (e.g., the sound signals include primarily music signals), and "Quiet" (e.g., the sound signals include minimal speech or noise signals). It is to be appreciated that these specific classifications are merely illustrative and that the ambient environment can also or alternatively be classified in other manners, such as a "Soft," a "Moderate," or "Loud," environment, etc. In certain embodiments, the body noise and environment analysis module 150 can also estimate the signal-to-noise ratio (SNR) of the external sound signals.

In one example, the body noise and environment analysis module 150 generates sound classification information/data 151, which includes/indicates at least the body noise classification(s) (i.e., the results of the analysis of the body noise(s) detected by the implantable sensors 144). As noted, in certain embodiments, the sound classification data 151 can also include the environment classification (i.e., the results of the analysis of the external sound signals detected by the implantable sensors 144) and, potentially, the SNR of the external sound signals. As such, in one illustrative example, the sound classification information/data 151 can indicate: "Quiet" (environmental classification), "low heartrate" (first body noise classification), and "deep breathing" (second body noise classification). In another illustrative example, the sound classification information/data 151 can indicate: "Loud" (environmental classification), "speaking" (first body noise classification), and "shallow breathing" (second body noise classification). These combinations of classifications are merely illustrative.

As noted above, in addition to the body noise and environment analysis module 150, the processing unit 118 also functionally includes a control module 152. The control module 152 is configured to use the sound classification data 151 to select, set, or otherwise determine a tinnitus therapy for the recipient, as a function of the recipient's body noises (e.g., determine an appropriate tinnitus therapy for the recipient, given the recipient's current ambient environment classification(s) and body noise classification(s)). Stated differently, the tinnitus therapy that is to be provided to the recipient is specifically determined based at least on one or more classifications of the recipient's body noises. As noted, in certain embodiments, the tinnitus therapy can also be determined based on one or more classifications of the ambient sound environment of the recipient and/or an SNR of the external acoustic sound signals.

In accordance with embodiments presented herein, the tinnitus therapy includes the delivery of stimulation signals (stimulation) to the recipient. These stimulation signals, sometimes referred to herein as "tinnitus therapy signals" or "tinnitus relief signals," can have a number of different forms and underlying objectives. For example, in certain embodiments, the tinnitus therapy signals can be masking signals that are configured to mask./cover the recipient's tinnitus symptoms (e.g., expose the recipient to sounds/noises at a loud enough volume that it partially or completely covers the sound of their tinnitus). In other embodiments, the tinnitus therapy signals can be distraction signals that are configured to divert the recipient's attention from the sound of tinnitus. In other embodiments, the tinnitus therapy signals can be habituation signals that are configured to assist the recipient's brain in reclassifying tinnitus as an unimportant sound that should can be consciously ignored. In still other embodiments, the tinnitus therapy signals can be neuromodulation signals that are configured to minimize the neural hyperactivity thought to be the underlying cause of tinnitus. In certain embodiments, the tinnitus therapy signals can be any combination of masking signals, distraction signals, habituation signals, and/or neuromodulation signals.

As noted, in the example of FIGS. 1A-1D and FIG. 2, the implantable tinnitus therapy device 100 includes an actuator 106 coupled to the recipient's ossicles 136. As such, in these examples, the tinnitus therapy signals, whether configured for masking, distraction, habituation, and/or neuromodulation purposes, are mechanical stimulation signals configured to cause motion of the fluid in the recipient's cochlea 138 (FIG. 1B). Shown in FIG. 2 is a tinnitus signal generator 160 that is configured to generate tinnitus therapy control signals (e.g., actuator control signals) 119 that drive the actuator 106 in a manner determined by the control module 152. That is, the tinnitus therapy control signals 119 are configured to cause the actuator 106 to vibrate in a selected manner. The tinnitus therapy signals delivered to the recipient are schematically represented in FIG. 2 by arrow 121.

The tinnitus therapy control signals 119 generated by the tinnitus signal generator 160 can dictate a number of different parameters for the tinnitus therapy signals 121. For example, the tinnitus therapy control signals 119 can be such that the tinnitus therapy signals 121 will be pure tone signals, multi tone signals, broadband noise, narrowband noise, low-pass filtered signals, high-pass filtered signals, band-pass filter signals, predetermined recordings, etc. The tinnitus therapy control signals 119 can also set modulations in the tinnitus therapy signals 121, transitions, etc. It is to be appreciated that these specific parameters are merely illustrative and that the tinnitus therapy signals 121 can have any of a number of different forms.

As described elsewhere herein, it is to be appreciated that use of mechanical stimulation signals for tinnitus therapy is merely illustrative of one technique that can be used in accordance with embodiments presented herein. In particular, in alternative arrangements, the tinnitus therapy signals can be electrical stimulation signals, mechanical stimulation signals delivered at a different location, electro-mechanical stimulation signals (e.g., electrical signals and mechanical signals delivered simultaneously or in close temporal proximity to one another), acoustic stimulation signals, electro-acoustic stimulation signals (e.g., electrical signals and acoustic signals delivered simultaneously or in close temporal proximity to one another), etc.

As noted above, the control module 152 is configured to determine the tinnitus therapy based on the sound classification data 151, which includes at least the body noise classification and, in certain embodiments, the environmental classification. In the specific example of FIG. 2, the processing unit 118 includes a tinnitus map module 154 that is configured to store a plurality of different tinnitus therapy maps 155. In general, each of the tinnitus therapy maps 155 is a set/collection of parameters that, when selected and used by the control module 152 and/or tinnitus signal generator 160, control the generation of the tinnitus therapy signals (e.g., used to generate tinnitus therapy control signals 119). The parameters can control the sound type (e.g., white noise, wave sounds, rain sounds, etc.), fluctuation rate, sound or masker level settings, on/off, pitch settings transition time settings, etc. In operation, different tinnitus therapy maps 155 can be created (e.g., by the software, an audiologist/clinician, through artificial intelligence, etc.) for different situations (i.e., different combinations of body noise classification(s) and environmental classifications). In operation, there will be maps for different therapies, such as specific maps for masking, specific maps for distraction, specific maps for habituation, specific maps for retraining, etc.

In the example of FIG. 2, the control module 152 is configured to analyze the sound classification data 151 (e.g., analyze the one or more body noise classifications and environmental classifications) and select one of the tinnitus therapy maps 155 for use in generating the tinnitus therapy signals delivered to the recipient. That is, in operation, the control module 152 is configured to select (e.g., using a neural network, artificial intelligence or machine learning engine, etc.) the most appropriate tinnitus therapy map for the recipient in the recipient's current "sound situation," where the current sound situation includes the recipient's currently present body noises and the attributes of the ambient environment. In accordance with embodiments presented herein, the recipient's current sound situation" is characterized by the one or more body noise classifications and, in certain embodiments, the one or more classifications of the ambient environment.

In certain examples, a selected tinnitus therapy map can be used to provide tinnitus therapy until the sound classification data 151 changes in manner that causes the control module 152 to select a different tinnitus therapy map. Once another tinnitus therapy map 155 is selected for use (for activation), the control module 152 will manage the transition between the maps to avoid unintended issues (e.g., annoyance to the recipient). For example, the device can select a map for retraining when the sound classification data 151 indicates a "Quiet" environment and "low breathing," which can mean that the recipient is relaxed and will be more receptive to that therapy. If the sound classification data 151 subsequently indicates a moderate music environment, then the device can switch to a masking therapy with low band pass modulated noise to not interfere with the music. If the sound classification data 151 subsequently indicates a "very low heart rate," "Quiet" environment," and "very low breathing," then the device can determine that the recipient is asleep and the tinnitus therapy can be temporarily paused to save power (e.g., stop tinnitus therapy automatically when the recipient has fallen asleep).

In another example, if the sound classification data 151 subsequently indicates "anxiety," the control module 152 can transition from, for example, retraining to relief therapy or masking instead. The detection of emotional reactions, in particular, can be used as a check to determine if a particular therapy is working by looking at, for example, heart rate or blood pressure changes when a particular therapy is activated. For example, the system can determine the recipient's emotional reactions to one or more tinnitus therapy signals. These emotional reactions can be stored and used as a part of an automated adaption process to adjust tinnitus therapy signals delivered to the recipient upon subsequent detection of the one or more body noise classifications.

As noted, FIG. 2 illustrates an example embodiment in which a plurality of predetermined tinnitus therapy maps 155 are stored and subsequently selected for use by the control module 152 and/or tinnitus signal generator 160. It is to be appreciated that a specific tinnitus therapy map can be selected in a number of different manners and that the selection can be based on information/data other than the sound classification data 151.

For example, initially, the control module 152 is programmed to select a specific tinnitus therapy map with specific sound classification data 151 (i.e., programmed to select a specific map for specific combinations of one or more body noise classifications and environmental classifications). In certain embodiments, the initial programming of control module 152 can be based on normative data for a population of different recipients. The initial programming of control module 152 to select a specific tinnitus therapy map can also or alternatively be based on predetermined selection settings that are set/determined for the recipient during a fitting session (e.g., a clinician directed session, a remote care session, etc.). That is, in certain embodiments, the initial programming of control module 152 is based preferences of the recipient, sometimes referred to herein as recipient-specific fitting data.

As noted above, the processing unit 118 also comprises a remote control module 158 and a learn and update module 156. The remote control module 158 and the learn and update module 156 are configured to update/adjust, over time, what tinnitus therapy map is selected by the control module 152 based, for example, in recipient preferences.

More specifically, the remote control module 158 is configured to receive recipient requests to change the tinnitus therapy. These recipient setting requests, which can be received wirelessly from a remote control device, external component, mobile application, etc., indicate the changes that the recipient wants to make some change to the tinnitus therapy (e.g., increase volume, change noise type, select different tinnitus relief map, etc.). The recipient's requested changes can be acted upon by the control module 152 to adjust, in real-time, the applied tinnitus therapy (i.e., change parameters of the tinnitus therapy signals 121 being delivered to the recipient).

In addition to being acted upon by the control module 152, recipient's requested changes are also provided to the learn and update module 156. The learn and update module 156 also has knowledge of body noise classification(s) and the environmental classifications(s) (e.g., has access to the sound classification data 151) and has knowledge of what tinnitus relief settings were being utilized (i.e., which tinnitus therapy map 155 was active) when the recipient requested the tinnitus setting changes. With this information, the learn and update module 156 is configured to implement an automated learning or adaption process to learn what tinnitus relief settings are preferred by the recipient in the presence of certain body noise classification(s) and environmental classifications(s).

The recipient preferences can be logged, over time, and analyzed relative to the body noise classification(s) and environmental classifications(s), again over time, and used to learn about the recipient's preferences and eventually adapt operation of the device according to the recipient's preferences (e.g., learn the recipient preferences and smoothly adapt the tinnitus relief therapy over the long-term based on the automated learning process). For example, the learn and update module 156 is configured to update the tinnitus therapy maps 155 and/or update operation of the control module 156 based on the automated learning process so that the recipient setting preference, in the presence of certain body noise classification(s) and environmental classification(s), is taken into consideration in the future (e.g., refine which map is selected for given body noise classifications). In other words, the learn and update module 156 is configured to automatically adjust operation of the processing unit 118 based on recipient preferences received during delivery of tinnitus therapy. This automated learning process can, for example, reduce the number of visits by the recipient to a clinic to adjust operation of the device. Data logging of the body noise classification(s) and environmental classification(s) and recipient interaction events can be saved and used, for example, by a clinician to evaluate the therapy progression of the recipient.

In certain embodiments, the learn and update module 156 will monitor the decision from the control module 152 (i.e., which map is selected) and any user inputs to update and/or create new maps based on event sequences. For instance, after some weeks, the recipient can feel that a masker level applied in a specific environment is too loud and, accordingly, will manually reduce the signal level (via user inputs received at the remote control module 158). As such, the implantable tinnitus therapy device 100 will automatically know what parameters need to be changed (according to the recipient preferences) and in which situation those changes should be made.

In addition, the learn and update module 156 can track the time spent in some therapy and make adjusts accordingly (e.g., decreasing the masking level or time in the long term). That is, the learn and update module 156 can determine and log (track and store) the attributes of tinnitus therapy signals delivered to the recipient over a period of time (e.g., time spent in particular therapies, characteristics of the particular therapies delivered to the recipient, etc.). This information can then be used as part of an automated adaption process to adjust tinnitus therapy signals delivered to the recipient upon subsequent detection of the one or more body noise classifications (e.g., adjust future therapy based on based on a time spent delivering tinnitus therapy signals to the recipient with particular attributes).

In certain examples, the learn and update module 156 can be implemented via a mobile/remote application implemented at an external device (e.g., mobile phone) in wireless communication with the implantable tinnitus therapy device 100. In such examples, the mobile application can obtain the logged data and a machine learning module in the application can update the maps and tinnitus control logic according to the recipient's preferences.

As noted, FIG. 2 illustrates an example embodiment in which a plurality of predetermined tinnitus therapy maps 155 are stored and subsequently selected for use by the control module 152 and/or tinnitus signal generator 160. It is to be appreciated that embodiments that select from among a plurality of predetermined tinnitus therapy maps 155 is merely illustrative and that other arrangements are possible. For example, in an alternative embodiment, the control module 152 or another entity can be configured to generate a selected tinnitus therapy map dynamically (e.g., in real-time) based on the sound classification data 151. In these embodiments, the selected tinnitus therapy map can be dynamically generated based on an analysis of logged recipient preferences, as described above.

As noted, FIGS. 1A-1E and 2 illustrate aspects of a stand-alone implantable tinnitus therapy device 100, sometimes referred to herein as an "invisible" acoustic tinnitus device. A stand-alone implantable tinnitus therapy device can be advantageous in that no external devices are required, which makes the device aesthetically pleasing, comfortable, and enables the recipient's ear canal to remain open for natural hearing. The stand-alone implantable tinnitus therapy device also enables around-the-clock therapy regimes, as desired, while utilizing adaptive learning of sound therapy adjustment to personalize operation of the device for the specific recipient. A stand-alone implantable tinnitus therapy device that is configured to stimulate the ear without introducing hearing loss (middle ear or bone) in an invisible manner with an implantable microphone can also function as a pathway to evolve into a hearing aid or other implantable device in the future (e.g., the implantable tinnitus therapy device can be a stepping stone to a middle ear implant, then to a cochlear implant).

Figure 3:
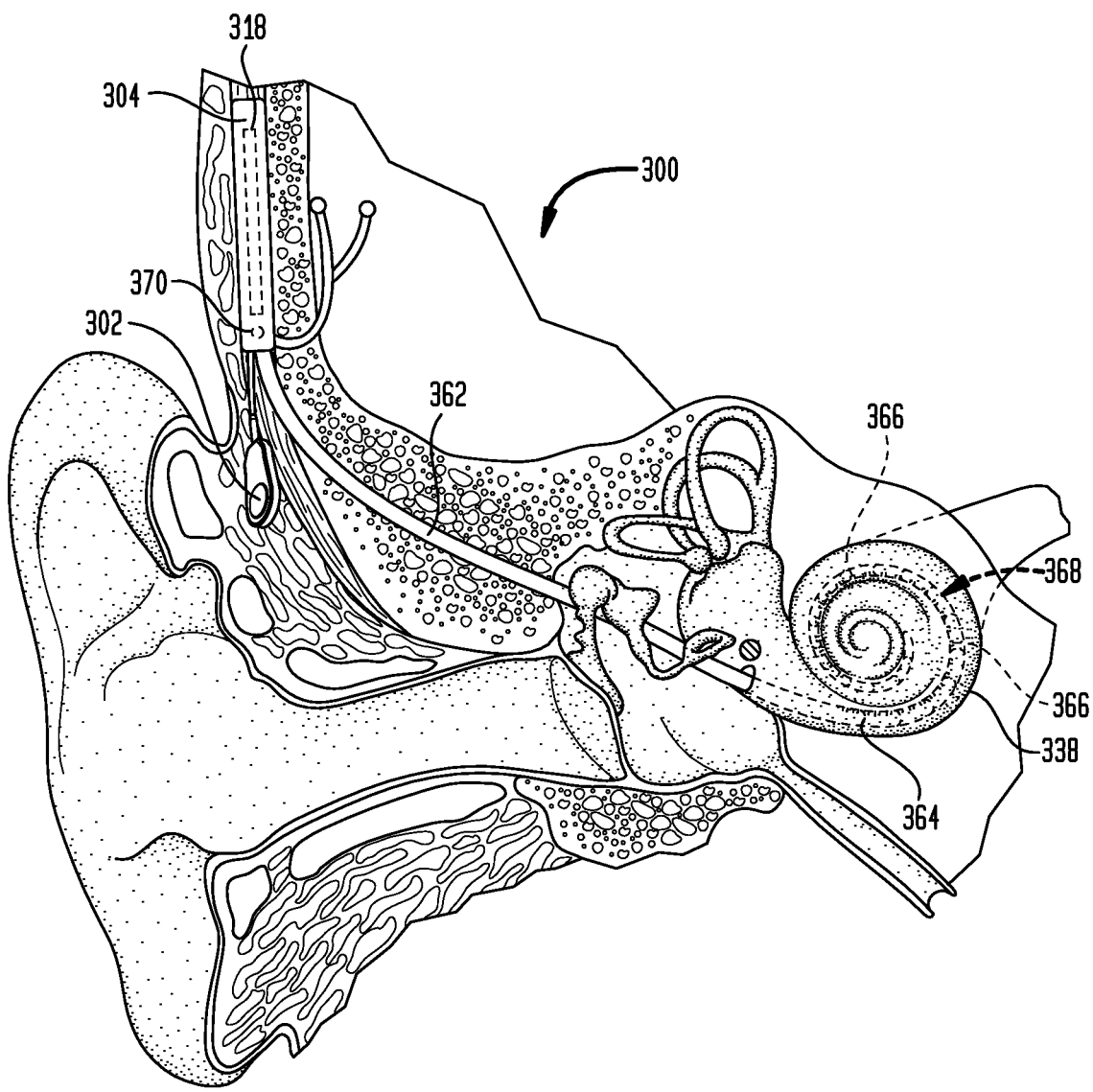
FIG. 3 is a schematic diagram illustrating a cochlear implant, in accordance with certain embodiments presented herein.

As described elsewhere herein, the tinnitus therapy techniques presented herein are not limited to stand-alone implantable tinnitus therapy devices, but instead can also or alternatively be incorporated as part of an auditory prosthesis, such as a cochlear implant, bone conduction device, middle ear auditory prosthesis, direct acoustic stimulator, auditory brain stimulator, etc. For example, FIG. 3 is schematic diagram of a "totally implantable cochlear implant" 300, meaning that all components of the cochlear implant are configured to be implanted under skin/tissue of a recipient. Because all components of cochlear implant 300 are implantable, the cochlear implant operates, for at least a finite period of time, without the need of an external device. An external device can be used to, for example, charge an internal power source (battery) of the cochlear implant 300.

The cochlear implant 300 comprises a sound input module 302, an implant body (main module) 304, a lead region 362, and an elongate intra-cochlear stimulating assembly 364 configured to be at least partially implanted in the recipient's cochlea 338. Stimulating assembly 364 includes a plurality of longitudinally spaced intra-cochlear electrical stimulating contacts (electrodes) 366 that collectively form a contact or electrode array 368 for delivery of electrical stimulation (current) to the recipient's cochlea.

The implant body 304 comprises a hermetically sealed housing in which a processing unit 318, a stimulator unit 370, radio frequency (RF) interface circuitry (not shown in FIG. 3), and at least one rechargeable battery (also not shown in FIG. 3) are disposed. The housing operates as a protective barrier between the electrical components within the housing (e.g., processing unit 318, stimulator unit 370, etc.) and the recipient's tissue and bodily fluid. The stimulating assembly 364 extends through an opening in the recipient's cochlea (e.g., cochleostomy, the round window, etc.) and has a proximal end connected to the stimulator unit via lead region 362 and a hermetic feedthrough (not shown in FIG. 3). Lead region 362 includes a plurality of conductors (wires) that electrically couple the electrodes 366 to the stimulator unit.

In the example of FIG. 3, the sound input unit 302 comprises one or more implantable sensors (e.g., accelerometer and microphone) configured to receive/detect body noises and external acoustic sound signals (external acoustic sounds). The processing unit 318 in the implant body 304 is configured to convert external acoustic sound signals detected at the sound input unit 302 into stimulation control signals for use in stimulating a first ear of a recipient. Stated differently, the processing unit 318 is configured to perform sound processing operations to convert the external acoustic sound signals into stimulation control signals that represent electrical stimulation for delivery to the recipient.

As noted, in addition to the processing unit, the implant body 304 also includes a stimulator unit 370. The stimulator unit 370 is configured to utilize the stimulation control signals (generated by the processing unit) to generate electrical stimulation signals that are delivered to the recipient's cochlea via one or more electrodes 366 of the electrode array 368.

In addition to the sound processing operations, the processing unit 318 is configured to perform tinnitus therapy operations, as described elsewhere herein. More specifically, the processing unit 318 is configured to configured to identify and classify/categorize body noises detected by the implantable sensors in the sound input unit 302 and to generate tinnitus therapy control signals based at least on the classification of the body noises. The tinnitus therapy control signals are provided to the stimulator unit 370 for use in delivering tinnitus therapy signals (tinnitus therapy) to the recipient. In the example of FIG. 3, the tinnitus therapy signals delivered to the recipient are electrical stimulation signals delivered via one or more of the electrodes 366. In certain examples the processing unit 318 is further configured to generate the tinnitus therapy control signals based the identified body noises and based on an acoustic environment of the recipient (e.g., based on a classification of the body noises and based on a classification of acoustic sound signals detected by the implantable sensors in the sound input unit 302).

Figure 4:
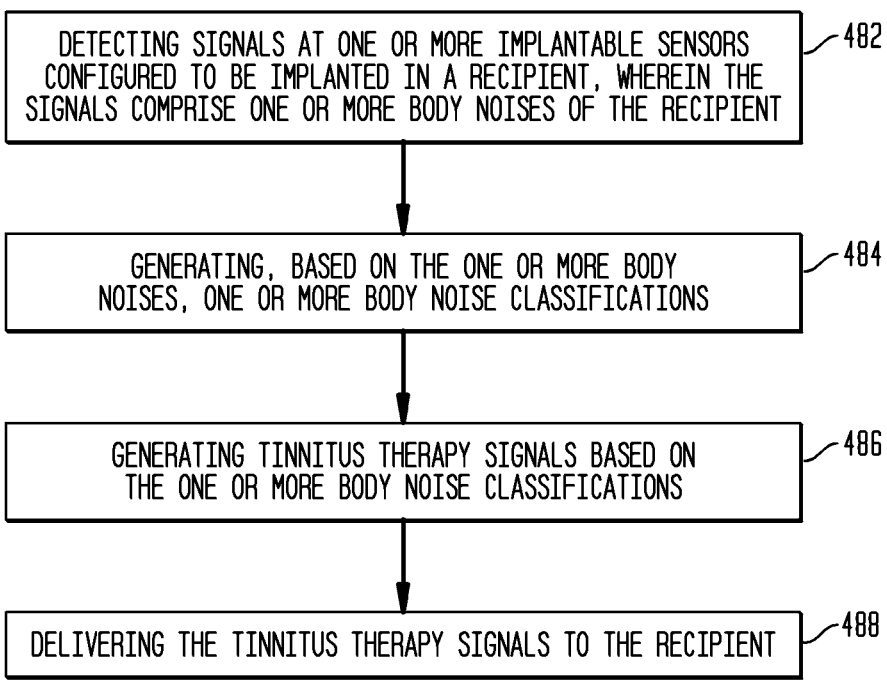
FIG. 4 is a high-level flowchart of a method, in accordance with certain embodiments presented herein.

FIG. 4 is a high-level flowchart of a method 480, in accordance with embodiments presented herein. Method 480 begins at 482 where one or more implantable sensors, which are configured to be implanted in a recipient, detect signals comprising one or more body noises of the recipient. At 484, one or more body noise classifications are generated based on the one or more body noises. At 486, tinnitus therapy signals are generated based on the one or more body noise classifications and, at 488, the tinnitus therapy signals are delivered to the recipient.

Figure 5:
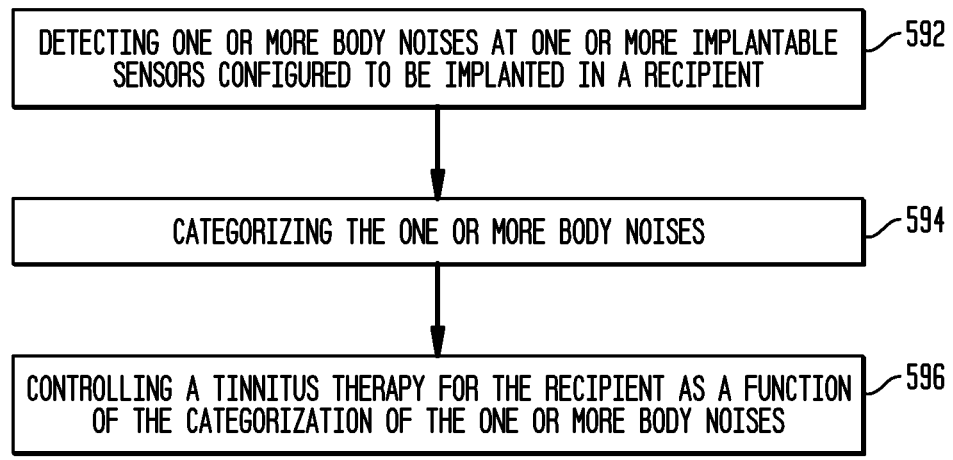
FIG. 5 is a high-level flowchart of another method, in accordance with certain embodiments presented herein.

FIG. 5 is a high-level flowchart of a method 590, in accordance with embodiments presented herein. Method 590 begins at 592 where one or more implantable sensors configured to be implanted in a recipient detect one or more body noises. At 594, the one or more body noises are categorized and, at 596, a tinnitus therapy for the recipient is controlled as a function of the categorization of the one or more body noises.

It is to be appreciated that the embodiments presented herein are not mutually exclusive and that the various embodiments can be combined with another in any of a number of different manners.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   detecting signals at one or more implantable sensors configured to be implanted in a recipient, wherein the signals comprise one or more body noises of the recipient;
   generating, based on the one or more body noises, one or more body noise classifications;
   generating tinnitus therapy signals based on the one or more body noise classifications; and
   delivering the tinnitus therapy signals to the recipient.

2. The method of claim 1, further comprising:
   detecting, with the one or more implantable sensors, one or more external acoustic sounds with the one or more body noises;
   generating, based on the one or more external acoustic sounds, one or more environmental classifications; and
   generating the tinnitus therapy signals based on the one or more body noise classifications and based on the one or more environmental classifications.

3. The method of claim 2, wherein generating the one or more body noise classifications comprises:
   simultaneously generating two or more different classifications of the one or more body noises.

4. The method of claim 1, wherein delivering the tinnitus therapy signals to the recipient comprises:
   generating, with an implantable actuator, mechanical vibration signals based on the one or more body noise classifications; and
   delivering the mechanical vibration signals to the recipient.

5. The method of claim 4, wherein delivering the mechanical vibration signals to the recipient, comprises:
   delivering the mechanical vibrations to an ossicular bone of the recipient.

6. The method of claim 4, wherein delivering the mechanical vibration signals to the recipient, comprises:
   delivering the mechanical vibration signals to a skull of the recipient.

7. The method of claim 1, wherein delivering the tinnitus therapy signals to the recipient comprises:
   generating electrical stimulation signals based on the one or more body noise classifications; and
   delivering the electrical stimulation signals to the recipient via one or more electrodes configured to be implanted in the recipient.

8. The method of claim 1, wherein generating the tinnitus therapy signals based on the one or more body noise classifications, comprises:
   selecting, based on the one or more body noise classifications, a first tinnitus therapy map from among a plurality of predetermined tinnitus therapy maps.

9. The method of claim 1, wherein the one or more body noise classifications indicate a current estimated behavior of the recipient.

10. The method of claim 1, further comprising:
    receiving a user input in response to delivery of the tinnitus therapy signals to the recipient, wherein the user input indicates a recipient adjustment to the tinnitus therapy signals; and
    adjusting the tinnitus therapy signals based on the user input.

11. The method of claim 10, further comprising:
    performing an automated adaption process to adjust, based on the user input, future tinnitus therapy signals delivered to the recipient upon subsequent detection of the one or more body noise classifications.

12. The method of claim 10, further comprising:
    performing an automated adaption process to adjust tinnitus therapy signals delivered to the recipient upon subsequent detection of the one or more body noise classifications based on emotional reactions of the recipient to one or more tinnitus therapy signals.

13. The method of claim 11, further comprising:
    logging attributes of tinnitus therapy signals delivered to the recipient over a period of time; and
    performing an automated adaption process to adjust tinnitus therapy signals delivered to the recipient upon subsequent detection of the one or more body noise classifications based on based on a time spent delivering tinnitus therapy signals to the recipient with particular attributes.

14. An apparatus, comprising:
    one or more implantable sensors configured to be implanted in a recipient, wherein the one or more implantable sensors are configured to detect one or more body noises of the recipient;
    a processing unit configured to:
       generate, based on the one or more body noises, one or more body noise classifications, and
       generate actuator control signals based on the one or more body noise classifications; and
    an implantable actuator configured to deliver tinnitus therapy signals to the recipient based on the actuator control signals.

15. The apparatus of claim 14, wherein the one or more implantable sensors are configured to detect one or more external acoustic sounds with the one or more body noises, and wherein the processing unit is configured to:
    generate, based on the one or more external acoustic sounds, one or more environmental classifications; and
    generating the actuator control signals based on the one or more body noise classifications and based on the one or more environmental classifications.

16. The apparatus of claim 14, wherein to generate the one or more body noise classifications, the processing unit is configured to:
    simultaneously generate two or more different classifications of the one or more body noises.

17. The apparatus of claim 14, further comprising:
    a memory configured to store a plurality of predetermined tinnitus therapy maps,
    wherein to generate the actuator control signals, the processing unit is configured to select, based on the one or more body noise classifications, a first tinnitus therapy map from among the plurality of predetermined tinnitus therapy maps.

18. The apparatus of claim 14, wherein the one or more body noise classifications indicate a current estimated behavior of the recipient.

19. The apparatus of claim 14, wherein the processing unit is configured to receive a user input in response to delivery of the tinnitus therapy signals to the recipient, wherein the user input indicates a recipient adjustment to the tinnitus therapy signals, and wherein the processing unit is configured to adjust the tinnitus therapy signals based on the user input.

20. The apparatus of claim 19, wherein the processing unit is configured to perform an automated adaption process to adjust, based on the user input, future tinnitus therapy signals delivered to the recipient in the presence of the one or more body noise classifications.

* * * * *